US00PP18096P2

(12) United States Plant Patent
Pieters

(10) Patent No.: US PP18,096 P2
(45) Date of Patent: Sep. 25, 2007

(54) ***CHRYSANTHEMUM* PLANT NAMED 'PPP TUSC 05'**

(50) Latin Name: *Chrysanthemum morifolium*
Varietal Denomination: PPP TUSC 05

(75) Inventor: Dirk Pieters, Oostnieuwkerke (BE)

(73) Assignee: Pieters Plant Production, Oostnieuwkerke (BE)

( * ) Notice: Subject to any disclaimer, the term of this patent is extended or adjusted under 35 U.S.C. 154(b) by 0 days.

(21) Appl. No.: 11/414,885

(22) Filed: Apr. 29, 2006

(51) Int. Cl.
*A01H 5/00* (2006.01)

(52) U.S. Cl. ..... Plt./287

(58) Field of Classification Search ..... Plt./287, Plt./290, 291
See application file for complete search history.

*Primary Examiner*—Kent Bell
*Assistant Examiner*—June Hwu

(57) ABSTRACT

A new and distinct *Chrysanthemum* plant cultivar is disclosed, characterized by large decorative type inflorescences, consistent flowering response to short days, blooming consistently after 49 days of short day length, salmon-pink ray florets, free branching habit, and a consistent natural season flowering habit during the last week of August.

1 Drawing Sheet

Latin name of the genus and species: *Chrysanthemum morifolium.*
Variety denomination: 'PPP TUSC 05'.

BACKGROUND OF THE INVENTION

The new cultivar 'PPP TUSC 05' is a product of a cross between the female parent 'GEDI TWO KIS' (U.S. Plant Pat. No. 14,996) and the male parent 'Orange Urano' (U.S. Plant Pat. No. 13,019). The new cultivar was discovered and selected by Dirk Pieters in September 2003 in Oostnieuwkerke, Belgium.

Asexual reproduction of the new cultivar 'PPP TUSC 05' by terminal cuttings and tissue culture was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP TUSC 05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP TUSC 05.' These characteristics in combination distinguish 'PPP TUSC 05' as a new and distinct *Chrysanthemum* cultivar:

1. Large salmon-colored inflorescence;
2. Consistent flowering response to short days, blooming consistently after 49 days of short day length;
3. Free branching habit; and
4. Consistent natural season flowering habit during the last week of August.

Plants of the new cultivar 'PPP TUSC 05' are similar to plants of the female parent variety, 'GEDI TWO KIS', which is also the most similar commercial variety to the new cultivar 'PPP TUSC 05', in most horticultural characteristics, however plants of the new cultivar 'PPP TUSC 05' are smaller in height than the female parent. Also, 'PPP TUSC 05' blooms about two weeks earlier than the female parent and the new cultivar has a longer inflorescence longevity. Additionally, the ray florets of the new cultivar are red-pink compared to the yellow-orange ray florets of the female parent. Finally, the new cultivar has a larger inflorescence diameter and less inflorescences per lateral branch than the female parent and commercially available variety.

Plants of the new cultivar 'PPP TUSC 05' are similar to plants of the male parent 'Orange Urano' in most horticultural characteristics, however, plants of the new cultivar 'PPP TUSC 05' are both taller and wider than the male parent. Also, the new cultivar has a longer inflorescence longevity. Additionally, the ray florets of the new cultivar are a red-pink compared to the orange-red of the male parent. Finally, there are far less disc florets on the new cultivar than on plants of the male parent 'Orange Urano.'

BRIEF DESCRIPTION OF THE PHOTOGRAPH

The accompanying photograph in FIG. 1 illustrates in full color a typical plant of 'PPP TUSC 05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP TUSC 05' plants grown in Oxnard, Ventura County, Calif., during the months of May through September 2005. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP TUSC 05.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 28.5 cm.
Plant spread: Approximately 52 cm.
Growth rate: Moderate.
Branching characteristics: Free Branching.
Length of lateral branches: Approximately 27 cm.
Number of leaves per lateral branch: Approximately 60.
Age of plant described: Approximately 120 days.

FOLIAGE

Leaf:
*Arrangement.*—Alternate single.
*Average length.*—Approximately 3.9 cm.
*Average width.*—Approximately 2.5 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 1.5 cm.
*Color.*—Young foliage upper side: Near Green 139A. Young foliage under side: Near Green 137B. Mature foliage upper side: Near Yellow-Green 147A. Mature foliage under side: Near Green 137A.
*Venation.*—Type: Palmately net. Venation color upper side: Near Green 138C. Venation color under side: Near Green 138C.
Petiole:
*Average length.*—Approximately 1 cm.
*Color.*—Near Green 137A.
*Diameter.*—Approximately 0.3 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately last week of August.
*Number of inflorescences per lateral branch.*—Approximately 46.
*Inflorescence diameter.*—Approximately 5.5 cm.
*Inflorescence depth.*—Approximately 2.3 cm.
*Inflorescence longevity on plant.*—Approximately 28 to 34 days.
*Persistence.*—Persistent.
Ray florets:
*Appearance.*—Matte.
*Texture.*—Smooth.
*Average number of ray florets per inflorescence.*—236.
*Shape.*—Oblanceolate.
*Aspect.*—Flat.
*Margin.*—Entire.
*Apex.*—Obtuse.
*Length.*—Approximately 1.8 cm.
*Width.*—Approximately 0.5 cm.
*Color.*—Upper surface at first opening: Near Red 47B. Upper surface at maturity: Near Red 54C. Upper surface at fading: Near Red-Purple 70D. Under surface at first opening: Near Red 54A. Under surface at maturity: Near Red 54D. Under surface at fading: Near Red-Purple 69A.
Disc florets:
*Appearance.*—Shiny.
*Texture.*—Smooth.
*Average number of florets per disc.*—Approximately 5.
*Shape.*—Cylindric.
*Apex.*—Obtuse.
*Average length.*—Approximately 0.4 cm.
*Average width.*—Approximately 0.1 cm.
*Color.*—At first opening: Near Yellow 9A. At maturity: Near Yellow 12A. At fading: Near Yellow 11A.
Peduncle:
*Length.*—At terminal end (shortest): Approximately 5.5 cm. At lateral end (longest): Approximately 7.5 cm.
*Angle to stem.*—Acute.
*Strength.*—Moderate.
*Color.*—Near Yellow-Green 144C.
*Habit.*—Upright.
*Diameter.*—Approximately 0.1 cm.
*Surface texture.*—Lightly pubescent.
Inflorescence bud:
*Length.*—Approximately 0.4 cm.
*Diameter.*—Approximately 0.6 cm.
*Form.*—Globular.
*Color.*—Near Green 138C.
Involucral bracts (phyllaries):
*Appearance.*—Matte.
*Texture.*—Lightly pubescent.
*Number.*—Approximately 25.
*Shape.*—Ovate.
*Margin.*—Entire.
*Apex.*—Acute.
*Length.*—Approximately 0.7 cm.
*Width.*—Approximately 0.3 cm.
*Color.*—Upper side: Near Green 137A. Under side: Near Green 137D.

REPRODUCTIVE ORGANS

Ray florets:
*Number of pistils per floret.*—1.
*Stigma shape.*—2 branched.
*Stigma color.*—Near Yellow 2.
*Style color.*—Near Green-Yellow 1C.
*Style length.*—Approximately 0.4 cm.
*Stamens.*—Absent.
Disc florets:
*Number of pistils per floret.*—1.
*Stigma shape.*—Cylindric.
*Stigma color.*—Near Yellow 7A.
*Style length.*—Approximately 0.1 cm.
*Style color.*—Near Yellow-Green 154C.
*Number of stamens per floret.*—Approximately 5.
*Anther shape.*—Tubular.

*Anther color.*—Near Yellow 8A.
*Pollen color.*—Near Yellow 8A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP TUSC 05' as herein illustrated and described.

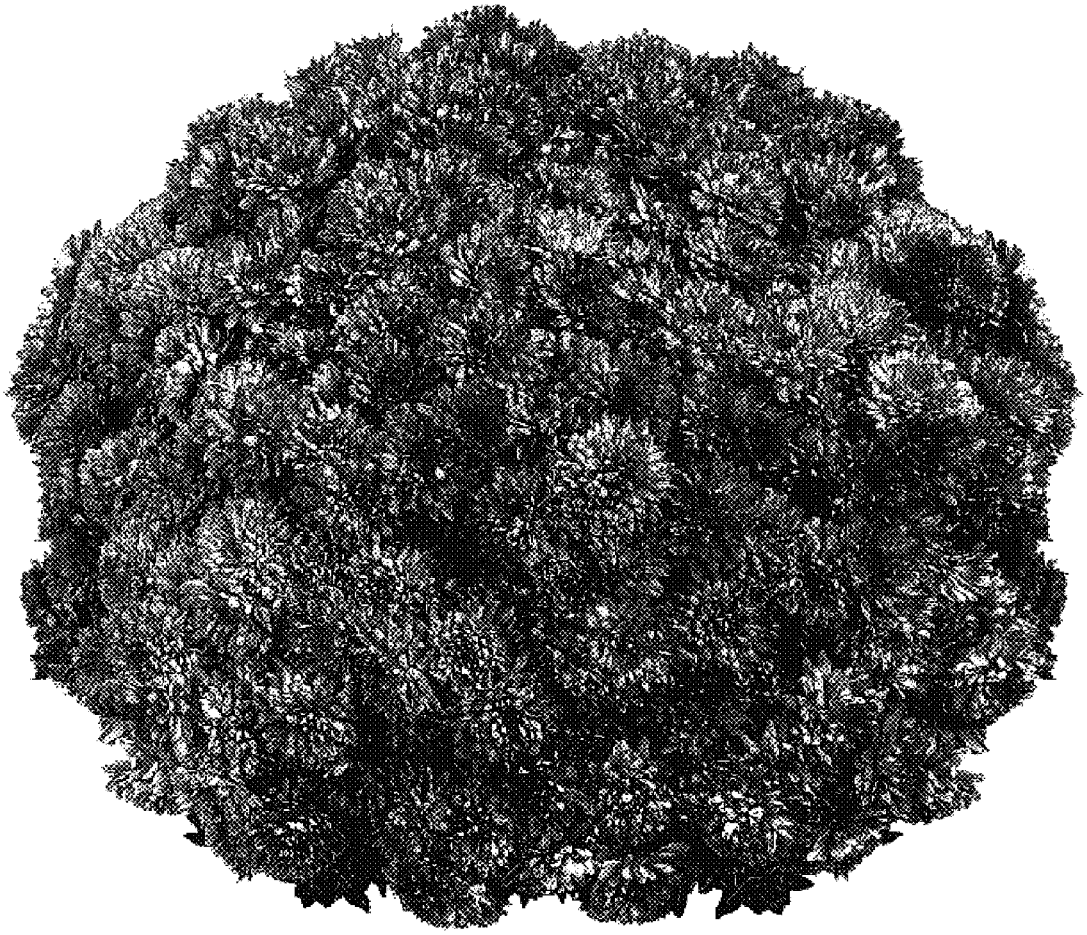

* * * * *